United States Patent

De Cicco et al.

(10) Patent No.: US 12,036,066 B2
(45) Date of Patent: Jul. 16, 2024

(54) IVUS AND EXTERNAL IMAGING TO MAP ANEURYSM TO DETERMINE PLACEMENT OF COILS AND LIKELIHOOD OF SUCCESS

(71) Applicant: KONINKLIJKE PHILIPS N.V., Eindhoven (NL)

(72) Inventors: Dino De Cicco, Ramona, CA (US); John Unser, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 671 days.

(21) Appl. No.: 16/100,429

(22) Filed: Aug. 10, 2018

(65) Prior Publication Data

US 2019/0046156 A1 Feb. 14, 2019

Related U.S. Application Data

(60) Provisional application No. 62/543,746, filed on Aug. 10, 2017.

(51) Int. Cl.
*A61B 8/00* (2006.01)
*A61B 6/00* (2006.01)
(Continued)

(52) U.S. Cl.
CPC ............ *A61B 8/0841* (2013.01); *A61B 6/032* (2013.01); *A61B 6/12* (2013.01); *A61B 6/4417* (2013.01);
(Continued)

(58) Field of Classification Search
CPC ....... A61B 8/0841; A61B 34/20; A61B 6/032; A61B 6/12; A61B 6/4417; A61B 8/0891;
(Continued)

(56) References Cited

U.S. PATENT DOCUMENTS 9,795,388 B1 * 10/2017 Evans ................ A61B 17/1214
2011/0319758 A1 * 12/2011 Wang ................. A61B 17/3403
600/439

(Continued)

OTHER PUBLICATIONS

Smith et al., IVUS-Directed Coil Embolization After Type B Aortic Dissection, Oct. 2009, Endovascular Today, https://evtoday.com/articles/2009-oct/1009_08-php.*

*Primary Examiner* — Shahdeep Mohammed
*Assistant Examiner* — Adam D. Kolkin

(57) ABSTRACT

Devices, systems, and methods for evaluating a vessel and tracking progression of an intravascular procedure are disclosed. In an embodiment, a medical system is disclosed. One embodiment of the medical system comprises a medical processing unit in communication with an intravascular device configured to obtain intravascular ultrasound (IVUS) data and with an external ultrasound device configured to obtain external ultrasound data. The medical processing unit is configured to receive the IVUS data from the intravascular device, wherein the intravascular device is positioned proximate to an aneurysm, receive the external ultrasound data from the external ultrasound device, wherein the external ultrasound device is positioned to image the aneurysm, and track progression of a coil embolization of the aneurysm based on the IVUS data and the external ultrasound data.

18 Claims, 6 Drawing Sheets

(51) Int. Cl.

| | | |
|---|---|---|
| *A61B 6/03* | (2006.01) | |
| *A61B 6/12* | (2006.01) | |
| *A61B 8/08* | (2006.01) | |
| *A61B 8/12* | (2006.01) | |
| *A61B 17/12* | (2006.01) | |
| *A61B 34/20* | (2016.01) | |
| *A61M 25/10* | (2013.01) | |
| *G16H 20/40* | (2018.01) | |
| *G16H 40/63* | (2018.01) | |
| *A61B 5/00* | (2006.01) | |
| *A61B 5/02* | (2006.01) | |
| *A61B 8/06* | (2006.01) | |
| *A61B 34/00* | (2016.01) | |
| *A61B 90/00* | (2016.01) | |

(52) U.S. Cl.
CPC .............. *A61B 8/0891* (2013.01); *A61B 8/12* (2013.01); *A61B 8/4416* (2013.01); *A61B 8/445* (2013.01); *A61B 8/4461* (2013.01); *A61B 8/4477* (2013.01); *A61B 17/12113* (2013.01); *A61B 17/1214* (2013.01); *A61B 34/20* (2016.02); *A61M 25/10* (2013.01); *G16H 20/40* (2018.01); *G16H 40/63* (2018.01); *A61B 5/0035* (2013.01); *A61B 5/02014* (2013.01); *A61B 8/06* (2013.01); *A61B 8/4483* (2013.01); *A61B 2017/1205* (2013.01); *A61B 2034/2063* (2016.02); *A61B 2034/252* (2016.02); *A61B 2090/367* (2016.02); *A61B 2090/378* (2016.02); *A61B 2090/3925* (2016.02); *A61B 2090/3966* (2016.02)

(58) Field of Classification Search
CPC ......... A61B 8/12; A61B 8/4416; A61B 8/445; A61B 8/4461; A61B 8/4477; A61B 7/12113; A61B 7/1214; A61B 2034/2063; A61B 34/252; A61B 2090/367; 2090/378; A61B 2090/3925; A61B 2090/3966; A61B 5/0035; A61B 5/02014; A61B 8/06; A61B 8/4483; A61B 2017/1205; G16H 20/40; G16H 40/63; A61M 25/10
See application file for complete search history.

(56) References Cited

U.S. PATENT DOCUMENTS

| | | | |
|---|---|---|---|
| 2012/0184642 A1* | 7/2012 | Bartling | A61B 5/0515 523/113 |
| 2012/0316436 A1* | 12/2012 | Lentz | A61M 25/0043 600/435 |
| 2013/0267848 A1* | 10/2013 | Fearnot | A61B 8/12 606/200 |
| 2016/0317328 A1* | 11/2016 | Berez | A61M 29/00 |
| 2017/0068792 A1* | 3/2017 | Reiner | A61B 5/0022 |
| 2017/0245864 A1* | 8/2017 | Franano | A61B 17/12109 |
| 2019/0212442 A1* | 7/2019 | Schatzberger | G01S 15/8936 |

* cited by examiner ic # IVUS AND EXTERNAL IMAGING TO MAP ANEURYSM TO DETERMINE PLACEMENT OF COILS AND LIKELIHOOD OF SUCCESS

FIELD

The present disclosure relates generally to the field of medical devices used in the assessment and treatment of disease within the circulatory system. Aspects of the present disclosure include using intravascular ultrasound (IVUS) in combination with external ultrasound to guide catheter placement and monitor progression of intravascular therapies.

BACKGROUND

Diseases of the circulatory system can be life-threatening and affect millions of people worldwide. One common problem is the accumulation of plaque inside a blood vessel. Over time, a buildup of plaque may occlude the blood vessel and adversely affect the flow of blood through said vessel. Plaque buildup is medically significant because it increases the likelihood of a blockage thereby putting the afflicted individual at an elevated risk of heart attack or stroke. Another common problem is the weakening of blood vessel walls. A weakened vessel may begin to bulge at the site of the weakness forming an aneurysm. While intact aneurysms are often asymptomatic, they may rupture at any time. Such ruptures can be deadly and are considered medical emergencies.

Given their severity and widespread occurrence, there remains a need for improved devices, systems, and methods for assessing and treating circulatory diseases. In that regard, the devices, systems, and associated methods of the present disclosure overcome one or more shortcomings of the prior art.

SUMMARY

Embodiments of the present disclosure include using intravascular ultrasound (IVUS) and external ultrasound to track progression of an intravascular therapy and determine the likelihood that the intravascular therapy will be successful. For example, in the case of coil embolization of an aneurysm, a medical processing system may receive intravascular ultrasound (IVUS) data from an intravascular device positioned proximate an aneurysm within the vasculature of a subject and may additionally receive external ultrasound data from an external ultrasound system positioned to image the aneurysm from outside the subject's body. The medical processing system may combine the IVUS data and the external ultrasound data to form images, e.g., three dimensional (3D) images, of the aneurysm. The resulting images may allow a physician overseeing delivery of coils into the aneurysm to observe their delivery and thereby track progression of the coil embolization procedure and ultimately determine the likelihood that the coil embolization will be successful. In some cases, the medical processing system itself may track progression of the coil embolization procedure and may output progress indicators to a display. Similarly, the medical processing system may determine the likelihood that the coil embolization will be successful and may output its determination to the display. Using combined IVUS and external ultrasound as described herein advantageously spares the subject from being exposed to potentially harmful radiation that accompanies radiation-based imaging procedures such as fluoroscopy.

In one embodiment, a medical system is disclosed. The medical system comprises a medical processing unit in communication with an intravascular device configured to obtain intravascular ultrasound (IVUS) data and with an external ultrasound device configured to obtain external ultrasound data. The medical processing unit is configured to receive the IVUS data from the intravascular device, wherein the intravascular device is positioned proximate to an aneurysm, receive the external ultrasound data from the external ultrasound device, wherein the external ultrasound device is positioned to image the aneurysm, and track progression of a coil embolization of the aneurysm based on the IVUS data and the external ultrasound data.

In some embodiments, the medical system further comprises the intravascular device. In some embodiments, the intravascular device comprises an IVUS transducer and is configured to perform the coil embolization of the aneurysm. In some embodiments, the medical system further comprises the external ultrasound device. In some embodiments, the medical processing unit is further configured to generate an image based on the IVUS data and the external ultrasound data. In some embodiments, the IVUS data and the external ultrasound data are combined to form a three dimensional (3D) image. In some embodiments, tracking progression of the coil embolization comprises analyzing the received IVUS data and the received ultrasound data, and further comprises comparing information gleaned from the analysis to information stored in a database storing information about past procedures. In some embodiments, tracking progression of the coil embolization comprises monitoring the progress of the intravascular device toward a therapy site. In some embodiments, tracking progression of the coil embolization comprises evaluating the completeness of the coil embolization.

In one embodiment, a method is disclosed. The method comprises receiving, at a medical processing unit, intravascular ultrasound (IVUS) data from an intravascular device positioned proximate to an aneurysm, receiving, at the medical processing unit, external ultrasound data from an external ultrasound device positioned to image the aneurysm, and tracking, by the medical processing unit, progression of a coil embolization of the aneurysm based on the IVUS data and the external ultrasound data.

In some embodiments, the method further comprises generating, by the medical processing unit, an image based on the IVUS data and the external ultrasound data. In some embodiments, generating the image comprises combining the IVUS data and the external ultrasound data to generate a three dimensional (3D) image. In some embodiments, the 3D image is an image of the aneurysm. In some embodiments, the IVUS data is obtained from within the aneurysm. In some embodiments, the external ultrasound data is obtained from an extravascular position aligned with the aneurysm. In some embodiments, tracking progression of the coil embolization includes monitoring the progress of the intravascular device toward a therapy site. In some embodiments, monitoring the progress of the intravascular device comprises mapping the location of the intravascular device within a vessel. In some embodiments, tracking progression of the coil embolization comprises evaluating the completeness of the coil embolization. In some embodiments, evaluating the completeness of the coil embolization comprises determining a level of embolic coil occlusion within the aneurysm. In some embodiments, the method further comprises determining, by the medical processing unit, a probability of success for the coil embolization based on the IVUS data and the external ultrasound data.

Additional aspects, features, and advantages of the present disclosure will become apparent from the following detailed description

BRIEF DESCRIPTIONS OF THE DRAWINGS

Illustrative embodiments of the present disclosure will be described with reference to the accompanying drawings, of which:

DETAILED DESCRIPTION

Figure 1:
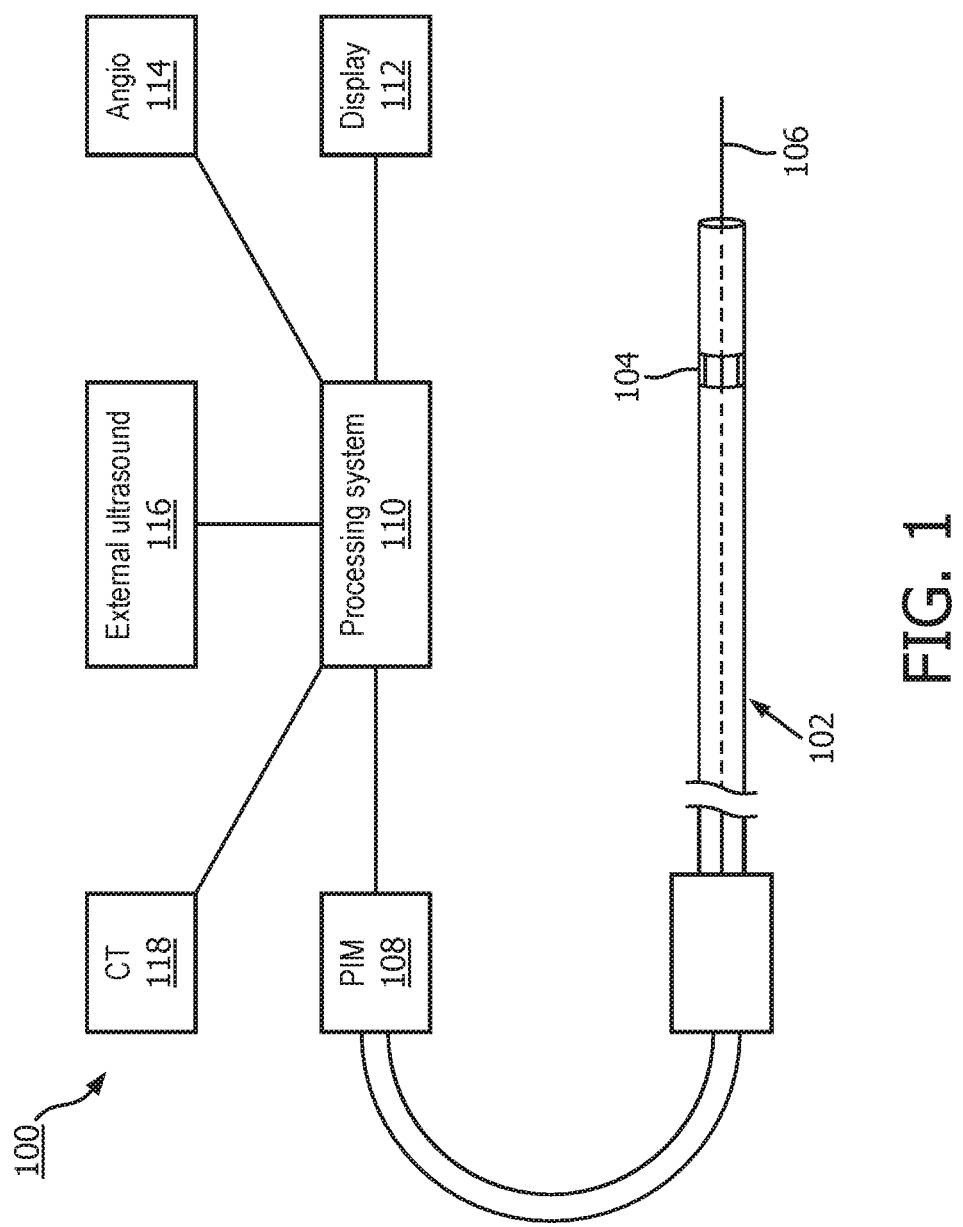
FIG. 1 is a schematic illustration of a system according to various aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. It is emphasized that, in accordance with the standard practice in the industry, some of the illustrated features may not be drawn to scale. In fact, the dimensions of various features may be arbitrarily increased or reduced for clarity. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure teaches using intravascular ultrasound (IVUS) and external ultrasound to track progression of an intravascular therapy and determine the likelihood that the therapy will be successful. Disease within the vasculature of the circulatory system may warrant medical intervention to treat and/or stop the progression of the disease. In some circumstances, the medical intervention may take the form of an intravascular therapy such as angioplasty, placement of a stent, ablation, embolization, aneurysm coiling, etc. In undertaking to perform an intravascular therapy, a physician may insert an intravascular instrument such as a guide wire or catheter into the vasculature of a subject. The physician may then navigate the intravascular instrument from the site of insertion to a diseased area. In order to facilitate navigation of the intravascular instrument to the diseased area, the physician may wish to be able to visualize the subject's vasculature.

In that regard, IVUS data obtained by the intravascular instrument may be combined with external ultrasound data to produce three dimensional (3D) images of the subject's vasculature which may help the physician navigate to the diseased area and may further allow the progression of the intravascular therapy to be monitored, assessed, or otherwise tracked by the physician and/or automatically by a medical processing unit. After the intravascular therapy has been completed, IVUS and external ultrasound may be used to determine the likelihood that the therapy will be successful. For example, in the case of an aneurysm coiling procedure, combined IVUS and external ultrasound may be used to determine whether blood flow to the aneurysm has been cut off or sufficiently reduced to allow the aneurysm to be clotted and sealed off from the main blood flow. One expected benefit of using combined IVUS and external ultrasound as described herein is that it advantageously spares the subject from being exposed to potentially harmful radiation that accompanies radiation-based imaging procedures such as fluoroscopy.

Turning now to FIG. 1, a system 100 is described. The system 100 comprises an intravascular instrument 102, a patient interface module (PIM) 108, a medical processing system 110, a display 112, an angiography system 114, an external ultrasound system 116, and a computed tomography (CT) system 118. In some circumstances, the system 100 may include additional elements and/or may be implemented without one or more of the elements illustrated in FIG. 1. For example, the system 100 may lack one or both of the angiography system 114 and the CT system 118. The intravascular instrument 102 comprises a transducer 104 and a lumen allowing passage of a treatment device 106 therethrough.

The system 100 may be deployed in a catheterization laboratory having a control room. The medical processing system 110 may be located in the control room. Optionally, the medical processing system 110 may be located elsewhere, such as in the catheterization laboratory itself. The catheterization laboratory may include a sterile field while its associated control room may or may not be sterile depending on the procedure to be performed and/or on the health care facility. The catheterization laboratory and control room may be used to perform any number of medical sensing procedures such as angiography, IVUS, virtual histology (VH), forward looking IVUS (FL-IVUS), intravascular photoacoustic (IVPA) imaging, a fractional flow reserve (FFR) determination, a coronary flow reserve (CFR) determination, optical coherence tomography (OCT), computed tomography, intracardiac echocardiography (ICE), forward-looking ICE (FLICE), intravascular palpography, transesophageal ultrasound, other medical sensing modalities, or combinations thereof.

The intravascular instrument 102, PIM 108, display 112, angiography system 114, external ultrasound system 116, and CT system may be communicatively coupled directly or indirectly to the medical processing system 110. These elements may be communicatively coupled to the medical processing system 110 via a wired connection such as a standard copper link or a fiber optic link and/or via wireless connections using IEEE 802.11 Wi-Fi standards, Ultra Wide-Band (UWB) standards, wireless FireWire, wireless USB, or another high-speed wireless networking standard. The medical processing system 110 may be communicatively coupled to one or more data networks, e.g., a TCP/IP-based local area network (LAN). In other embodiments, different protocols may be utilized such as Synchronous Optical Networking (SONET). In some cases, the medical processing system 110 may be communicatively coupled to a wide area network (WAN). The medical processing system 110 may utilize network connectivity to access various resources. For example, the medical processing system 110 may communicate with a Digital Imaging and Communications in Medicine (DICOM) system, a Picture Archiving and Communication System (PACS), and/or a Hospital Information System via a network connection.

The PIM 108 may be operable to receive medical sensing data, e.g., IVUS data, collected by the intravascular instrument 102 and to transmit the received data to the medical processing system 110. In an embodiment, the PIM 108 may transmit the medical sensing data over a Peripheral Component Interconnect Express (PCIe) data bus connection, over a Universal Serial Bus (USB) connection, over a Thunderbolt connection, over a FireWire connection, or over some other high-speed data bus connection. The PIM 108 may comprise one or more analog to digital (A/D) converters and may transmit digital data to the medical processing system 110. The PIM 108 may additionally or alternatively transmit analog data to the medical processing system 110.

The intravascular instrument 102 may be configured to be inserted into the vasculature of a subject. The subject may a person or other living organism suffering from one or more circulatory diseases for which intravascular intervention may be appropriate. The intravascular instrument 102 may comprise any form of device, instrument, or probe sized and shaped to be positioned within a vessel. In that regard, the intravascular instrument 102 may comprise a catheter and/or a guide wire. Generally, the intravascular instrument 102 may comprise a flexible elongate member including proximal and distal portions, a torque device to facilitate manipulation of a distal end of the intravascular instrument 102, e.g., to enable the intravascular instrument 102 to be steered through a tortuous vasculature, a connector configured to enable the intravascular instrument 102 to be coupled to an interface device such as the PIM 108 or a pullback device, or any combination thereof.

In some cases, the intravascular instrument 102 may include one or more echogenic regions. For example, a distal portion of the intravascular instrument 102 may comprise a series of alternating echogenic and non-echogenic regions. The echogenic regions may form a pattern recognizable to a physician and/or detectable by the medical processing system 110. The intravascular instrument 102 may be formed of echogenic material and/or may comprise an echogenic outer coating, film, sheath, or combinations thereof. The outer coating, film, and sheath may be composed entirely of echogenic material or may be rendered echogenic by inclusion of echogenic material, e.g., in the form of flakes, specks, particles, etc., in an otherwise non-echogenic or less echogenic substrate. In particular, it is contemplated that calcium may be used as an echogenic material. The one or more echogenic regions may increase the visibility of the intravascular instrument 102 within a vessel when external ultrasound is used to facilitate navigation of the intravascular instrument 102 through a subject's vasculature and/or to track progression of an intravascular therapy.

As illustrated in FIG. 1, the intravascular instrument 102 comprises a transducer 104, which may comprise an IVUS transducer, and which may be located at a distal portion of the intravascular instrument 102. The transducer 104 may be configured to both emit ultrasound signals and receive the reflected ultrasound signals (echoes). The emitted ultrasound signals, sometimes referred to as ultrasound pulses, pass through most tissues and blood but are partially reflected by discontinuities arising from tissue structures (such as the various layers of the vessel wall), red blood cells, and other features of interest. The ultrasound echoes may be processed, e.g., by the medical processing system 110, to form a cross-sectional image of structures within a vessel. The transducer 104 may comprise a piezoelectric micromachined ultrasonic transducer ("PMUT") transducer and associated circuitry, such as an application-specific integrated circuit (ASIC). In some instances, the transducer 104 may be housed within a transducer housing.

In some embodiments, the transducer 104 may comprise an array of transducers. The array may comprise any number of transducers, and in some particular embodiments may comprise 64 transducers. The array of transducers may be distributed about a circumference of the intravascular instrument 102 and may be connected to an electronic multiplexer circuit. The electronic multiplexer circuit may select transducers from the array for transmitting ultrasound signals and receiving reflected ultrasound signals. By stepping through a sequence of transmit-receive transducer pairs, the intravascular instrument 102 can synthesize the effect of a mechanically scanned transducer element, but without moving parts. Thus, the transducer array may be placed in direct contact with blood and vessel tissue with minimal risk of vessel trauma.

Alternatively, the transducer 104 may comprise a single transducer located on a flexible driveshaft that spins inside a sheath. The transducer may be oriented such that the ultrasound signals propagate generally perpendicular to an axis of the intravascular instrument 102. A fluid-filled (e.g., saline-filled) sheath may protect vessel tissue from the spinning transducer and driveshaft while permitting ultrasound signals to freely propagate from the transducer into the tissue and back. As the driveshaft rotates (for example, at 30 revolutions per second), the transducer may be periodically excited with a high voltage pulse to emit a short burst of ultrasound. The same transducer may then listen for returning ultrasound signals reflected from various tissue structures, and a two dimensional image of the vessel cross-section may be formed by the medical processing system 110 from a sequence of several hundred of these ultrasound pulse/echo acquisition sequences occurring during a single revolution of the transducer.

The intravascular instrument 102 may be configured to obtain medical data from within the vasculature of a subject. For example, the intravascular instrument 102 may obtain images, e.g., IVUS images, pressure data, flow data, etc., or combinations thereof. The intravascular instrument 102 may be configured to perform one or more intravascular therapies such as recanalization, stenting, ablation, embolization, aneurysm coiling, balloon angioplasty, etc., or combinations thereof. In that regard, the intravascular instrument 102 may be configured to deliver one or more treatment devices 106 to a diseased location within a vessel. Treatment device 106 may comprise a stent, a balloon, an embolization slurry, an aneurysm coil, a radiofrequency emitter, a cutting tool, or combinations thereof. It is specifically contemplated that the intravascular instrument 102 may be configured to both obtain medical data from within the vasculature of a subject and perform one or more intravascular therapies. In particular, the intravascular instrument 102 may be configured to both obtain IVUS images, e.g., via the transducer 104, and perform an aneurysm coiling procedure. In some cases, the intravascular instrument 102 may be configured to obtain IVUS images, perform an aneurysm coiling procedure, and place a stent—all of which may be done in a single trip without removal of the intravascular instrument 102 from the subject's vasculature.

The medical processing system 110 may comprise a computer workstation, mainframe, server, or any other type of computing system operable to process medical sensing data. The medical processing system 110 may comprise at least one processor such as a microcontroller or a dedicated central processing unit (CPU), a non-transitory computer-readable storage medium such as a hard drive, a random access memory (RAM), and/or compact disk read only memory (CD-ROM), a video controller such as a graphics processing unit (GPU), a network communication device, or any combination thereof. The medical processing system 110 may be located within a catheterization laboratory, within a control room associated with the catheterization laboratory, in another building, etc. The medical processing system 110 may receive, directly or indirectly, medical data from the intravascular instrument 102 and/or other elements of the system 100, e.g., the external ultrasound system 116. The medical processing system 110 may process the received medical data and output images generated based on the received medical data to the display 112. The display 112 may comprise multiple screens, and different screens may be configured to display different images. In some cases, the display 112 may be representative of a user interface (UI) that provides a physician user feedback about a procedure. As described herein, the medical processing system 110 may output recommendations about a procedure to the display 112. Such recommendations may overlay one or more images generated based on data gathered by one or more imaging modalities, e.g., IVUS and/or external ultrasound.

A subject suffering from one or more circulatory diseases, e.g., stenosis, aneurysm, arrhythmia, blood clots, etc., may benefit from receiving one or more intravascular therapies, e.g., recanalization, stenting, ablation, embolization, aneurysm coiling, balloon angioplasty, etc. In that regard, it may be beneficial to insert the intravascular instrument 102 into the vasculature of the subject and navigate the intravascular instrument 102 to a diseased location within the vasculature to allow the intravascular instrument 102 to collect medical data and/or perform an intravascular therapy, e.g., by utilizing treatment device 106. In some circumstances, the angiography system 114 and/or the CT system 118 may be used to obtain images of the subject's vasculature which may be used as a roadmap by a physician or operator of the intravascular instrument 102 to advance the intravascular instrument 102 through the vasculature to the diseased location. While the images produced by the angiography system 114 and/or the CT system 118 may be useful to the physician, the subject may be exposed to harmful radiation during the imaging process.

In order to limit the subject's exposure to radiation, it may be beneficial to use external ultrasound in conjunction with IVUS when navigating the intravascular instrument 102 to the diseased location and/or to track the progress of an intravascular therapy being performed at the diseased location. In addition to limiting the subject's radiation exposure, using external ultrasound in conjunction with IVUS advantageously allows intravascular therapies to be performed without radiation shields and radiation equipment which can lower the cost of performing the procedure resulting in savings for the subject and the treatment facility. Furthermore, substituting ultrasound for radiation may allow intravascular therapies to be performed bedside thereby reducing the number of times the subject is moved, which can be of particular importance in the event that the subject suffered a trauma.

The intravascular instrument 102 may be positioned within the subject's vasculature while a collector element of the external ultrasound system 116 may be positioned outside the subject's body, or extravascularly, at a location aligned with the intravascular instrument 102. As the intravascular instrument 102 moves through the subject's vasculature, the collector element may likewise be moved so as to maintain its alignment with the intravascular instrument 102. The collector element may be sized and shaped for grasping by the hand of an operator, e.g., a physician, and may be configured to transmit ultrasound signals and receive ultrasound echoes which may be used to form ultrasound images. The ultrasound images from the collector element may be used to form a longitudinal image of the vessels through which the intravascular instrument 102 is moving. The medical processing system 110 may display the longitudinal image and a physician may use the longitudinal image for reference as the intravascular instrument 102 is advanced through the subject's vasculature.

In some cases, the intravascular instrument 102 may collect IVUS data from within the vasculature while the external ultrasound system 116, e.g., via the collector element, collects external ultrasound data from outside the vasculature. It is noted that the term "external ultrasound data" as used herein describes ultrasound data that is collected from outside the subject's body, e.g., by the collector element, and is not limited to data about external structures but rather includes data about internal structures, e.g., the subject's vasculature. The IVUS data and the external ultrasound data may be displayed on display 112. In some cases, the IVUS data and the external ultrasound data may be displayed independently, e.g., on different screens. In other cases, the IVUS data and the external ultrasound data may be coregistered or otherwise displayed together. In particular, the IVUS data and the external ultrasound data may be combined, e.g., by the medical processing system 110, to form 3D images of the subject's vasculature including of a diseased location such as an aneurysm, stenosis, etc. A physician may use the 3D images for reference as the intravascular instrument 102 is advanced through the subject's vasculature. In some cases, IVUS data and external ultrasound data may be collected throughout, or at certain points before, during, and/or after, an intravascular therapy. In such cases, the 3D images formed from the combined IVUS data and external ultrasound data may be used, e.g., by the medical processing system 110 and/or by the physician, to track the progress of the intravascular therapy and/or to determine the likelihood that the intravascular therapy will be successful.

The medical processing system 110 may receive IVUS data from the intravascular instrument 102, may receive external ultrasound data from the external ultrasound system 116, and may map the location of the intravascular instrument 102 within the vasculature, e.g., by forming a 3D image, based on the IVUS data and the external ultrasound data. The medical processing system 110 may further monitor or track the progress of the intravascular instrument 102 as it is advanced toward the diseased location. Once an intravascular therapy has commenced at the diseased location, the medical processing system 110 may track the progression of the intravascular therapy based on the IVUS data and the external ultrasound data, e.g., based on an analysis of a 3D image generated from the IVUS data and the external ultrasound data.

Tracking progression of the intravascular therapy may include evaluating the completeness of the intravascular therapy. In some cases, the medical processing system 110 may output recommendations to the display 112 based on its evaluation of the completeness of the intravascular therapy. For example, the medical processing system 110 could evaluate the completeness of an aneurysm coiling procedure by determining a level of coil occlusion within the aneurysm. The medical processing system 110 may then output a recommendation whether or not to continue delivering coils into the aneurysm to the display 112 based on the level of coil occlusion. The recommendation may overlay one or more of an IVUS image, an external ultrasound image, or a 3D image formed based on IVUS data and external ultrasound data.

In some embodiments, the IVUS data and/or the external ultrasound data may be coregistered with the 2D or 3D CT image, which would further improve placement accuracy and decrease procedural time. The outcome of coil placement will be verified with this multi-imaging system, which will improve outcomes vs. standard fluoroscopic guidance. In some embodiments, the IVUS mounted delivery catheter is tracked to the aneurysm as identified on a CT image and/or angiogram.

Evaluating the completeness of the intravascular therapy may comprise parsing a database that stores information on one or more intravascular therapies, including past procedures, and comparing information stored in the database with information gleaned from the IVUS data and external ultrasound data, including information gleaned from an analysis of a 3D image generated from the IVUS data and external ultrasound data. In that regard, the medical processing system 110 may comprise and/or be in communication with a database that stores information on one or more intravascular therapies, including what constitutes completion of the therapy. For example, the database include information that indicates an aneurysm coiling procedure is considered complete when blood flow to the aneurysm is reduced to about 30% of pre-treatment levels, to about 25% of pre-treatment levels, to about 20% of pre-treatment levels, to about 15% of pre-treatment levels, to about 10% of pre-treatment levels, to about 5% of pre-treatment levels, is reduced below a certain pressure, is reduced sufficiently to allow clotting, is reduced below a certain total volume, is reduced below about 30% of the volume of the aneurysm, is reduced below about 25% of the volume of the aneurysm, is reduced below about 20% of the volume of the aneurysm, is reduced below about 15% of the volume of the aneurysm, is reduced below about 10% of the volume of the aneurysm, is reduced below about 5% of the volume of the aneurysm, when blood flow is shut off entirely, when coils fill about 50% of the aneurysm, when coils fill about 60% of the aneurysm, when coils fill about 70% of the aneurysm, when coils fill about 75% of the aneurysm, when coils fill about 80% of the aneurysm, when coils fill about 85% of the aneurysm, when coils fill about 90% of the aneurysm, when coils fill about 95% of the aneurysm, when coils fill about 100% of the aneurysm, when coils fill 100% of the aneurysm, or combinations thereof. The medical processing system 110 may be able to determine one or more of blood flow, blood pressure, blood volume, and what percent of the aneurysm is filled with coils based on an analysis of IVUS data and external ultrasound data, e.g., an analysis of a 3D image generated from IVUS data and external ultrasound data.

Accordingly, in the case of an aneurysm coiling procedure, the medical processing system 110 may receive IVUS data and external ultrasound data from which one or more of blood flow, blood pressure, blood volume, blood pressure, what percent of the aneurysm is filled with coils, or combinations thereof may be determined and cross referenced with the database. The medical processing system 110 may determine the completeness of the procedure based on the result of the cross reference. For example, if an aneurysm coiling procedure is considered complete when 100% of the aneurysm is filled with coils, and analysis of the IVUS data and external ultrasound data, e.g., analysis of a 3D image generated from the IVUS data and external ultrasound data, indicates that 80% of the aneurysm is so filled, the medical processing system 110 may determine that the aneurysm coiling procedure is 80% complete. The medical processing system 110 may display the result of such a completion analysis on the display 112, e.g, by overlaying the result on one or more images generated based on IVUS data and/or external ultrasound data.

The metrics used to determine what constitutes a completed intravascular therapy may be established, in some cases by the medical processing system 110, based historical data of past procedures, e.g., data indicating the point at which past successful procedures were stopped. For example, the historical data of past procedures may indicate that, for aneurysm coiling procedures, all past successful procedures were stopped at a point in which at least 90% of the aneurysm was filled with coils. For the given the example, it may be established, e.g., by the medical processing system 110, that the threshold for completion of an aneurysm coiling procedure is 90% occlusion of the aneurysm with coils. The medical processing system 110 may automatically update the database after each intravascular therapy has been performed. For example, at the conclusion of an intravascular therapy, the medical processing system 110 may log details about the intravascular therapy in the database, including whether the intravascular therapy was successful, when the intravascular therapy was stopped, etc. Existing entries may be updated if, for example, an intravascular therapy previously recorded as successful ultimately failed within a certain threshold of time.

The medical processing system 110 may evaluate the completeness of an intravascular therapy in response to a command by a physician or operator, automatically at predetermined intervals, e.g., every 0.5 seconds, every second, every 2 seconds, every 3 seconds, every 5 seconds, every 10 seconds, every 15 seconds, every 20 seconds, every 25 seconds, every 30 seconds, every minute, every 1.5 minutes, every 2 minutes, every 5 minutes, or combinations thereof, automatically after certain events, e.g., coil detachment, stent placement, irradiation bursts, treatment device changes, or combinations thereof, automatically as data is received, or combinations thereof. The medical processing system 110 may display the level of completeness of the intravascular therapy on the display 112 and may update the level of completeness in response to a command by a physician or operator, automatically at predetermined intervals, e.g., every 0.5 seconds, every second, every 2 seconds, every 3 seconds, every 5 seconds, every 10 seconds, every 15 seconds, every 20 seconds, every 25 seconds, every 30 seconds, every minute, every 1.5 minutes, every 2 minutes, every 5 minutes, or combinations thereof, automatically after certain events, e.g., coil detachment, stent placement, irradiation bursts, treatment device changes, or combinations thereof, automatically as completeness analyses are completed, or combinations thereof. Upon determining that the intravascular therapy is complete, the medical processing system 110 may automatically provide an indication or prompt to that effect. In that regard, the indication or prompt may comprise a change in screen color, an audible tone, display of an image, haptic feedback, display of a text box, or combinations thereof.

The medical processing system 110 may determine a probability or likelihood of success for an intravascular therapy based on an analysis of IVUS data and external ultrasound data, e.g., based on an analysis of a 3D image generated from the IVUS data and the external ultrasound data. Analyzing the IVUS data and external ultrasound data may comprise comparing information gleaned from the IVUS data and external ultrasound data with information contained in a database storing information about one or more intravascular therapies, including information about past procedures. In that regard, the medical processing system 110 may comprise or be in communication with a database which includes information about one or more intravascular therapies, including information about past procedures. The information about past procedures may include whether or not the past procedures were successful and information about the state of those procedures when they were stopped. For example, in the event that information stored in the database indicates that 90% of past aneurysm coiling procedures in which at least 98% of the aneurysm was filled with coils were successful, the medical processing system 110 may determine that a present aneurysm coiling procedure in which 98% of the aneurysm is filled with coils has a 90% probability of success.

Determining probability or likelihood of success may be based on a plurality of factors, each of which may be assigned a weight. Such factors may include factors used in determining completeness of the intravascular therapy but may be weighted differently in a determination of likelihood of success versus a determination of completeness. In that regard, it should be understood that while completeness and likelihood of success are related, they are not synonymous. For example, an aneurysm coiling procedure may be considered complete when a certain percentage of the aneurysm is filled with coils but may nevertheless be considered a failed procedure if the aneurysm ruptures before blood flow to the aneurysm is stopped. In the given example, what percentage of the aneurysm is filled with coils may be relevant to both determining completeness and determining likelihood of success but may be superseded in importance by the rupture when determining likelihood of success. Furthermore, one or more factors may be used in determining likelihood of success that are not used in determining completeness and vice versa. For example, location of an aneurysm may be a factor in determining the likelihood of success of an aneurysm coiling procedure but may be irrelevant to determining the completeness of the aneurysm coiling procedure.

The medical processing system 110 may determine the likelihood of success of an intravascular therapy in response to a command by a physician or operator, automatically at predetermined intervals, e.g., every 0.5 seconds, every second, every 2 seconds, every 3 seconds, every 5 seconds, every 10 seconds, every 15 seconds, every 20 seconds, every 25 seconds, every 30 seconds, every minute, every 1.5 minutes, every 2 minutes, every 5 minutes, or combinations thereof, automatically after certain events, e.g., coil detachment, stent placement, irradiation bursts, treatment device changes, or combinations thereof, automatically as data is received, automatically after determining that the intravascular therapy is complete, or combinations thereof. The medical processing system 110 may display the likelihood of success of the intravascular therapy on the display 112 and may update the likelihood of success in response to a command by a physician or operator, automatically at predetermined intervals, e.g., every 0.5 seconds, every second, every 2 seconds, every 3 seconds, every 5 seconds, every 10 seconds, every 15 seconds, every 20 seconds, every 25 seconds, every 30 seconds, every minute, every 1.5 minutes, every 2 minutes, every 5 minutes, or combinations thereof, automatically after certain events, e.g., coil detachment, stent placement, irradiation bursts, treatment device changes, or combinations thereof, automatically after a determination that the intravascular therapy is complete, or combinations thereof. The medical processing system 110 may display the likelihood of success of the intravascular therapy adjacent to the level of completeness, on a different screen than the level of completeness, side-by-side with the level of completeness, on top of the level of completeness, below the level of completeness, or in replacement of the level of completeness.

In some cases, the medical processing system 110 may output a recommendation to the display 112 based on the likelihood of success. For example, if the medical processing system 110 determines that an intravascular therapy is unlikely to be successful, it may recommend follow up action. The medical processing system 110 may identify the follow up action based on a parsing of a database storing information about follow up actions that have been performed in past unsuccessful procedures. In parsing the database, the medical processing system 110 may filter out follow up actions that were unsuccessful. For example, the medical processing system 110 may limit its consideration of follow up actions to follow up actions performed in past unsuccessful procedures where the follow up action was successful.

Turning now to FIGS. 2A-G, shown therein is the intravascular instrument 102 disposed within a blood vessel 202 having an aneurysm 204 while the external ultrasound system 116, e.g., the collector element of the external ultrasound system 116, is located outside a subject's body against the subject's skin 206 at a positioned aligned with the aneurysm 204. FIGS. 2A-G illustrate various stages of an intravascular therapy, specifically an aneurysm coiling procedure. Said intravascular therapy may be performed by or with one or more elements of the system 100 described herein.

Figure 2A:
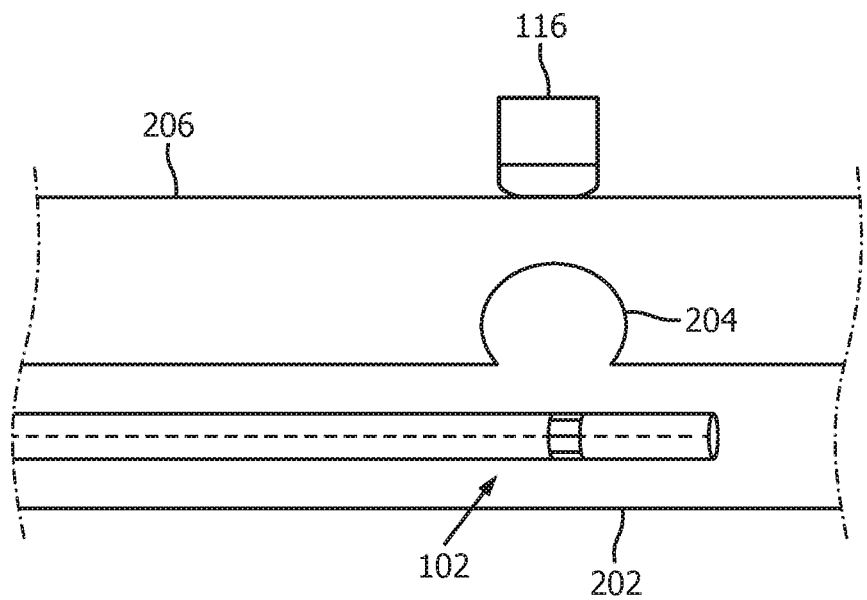
FIG. 2A is a diagrammatic, cross-sectional view of a portion of a subject's anatomy during an intravascular therapy according to various aspects of the present disclosure.
Figure 2B:
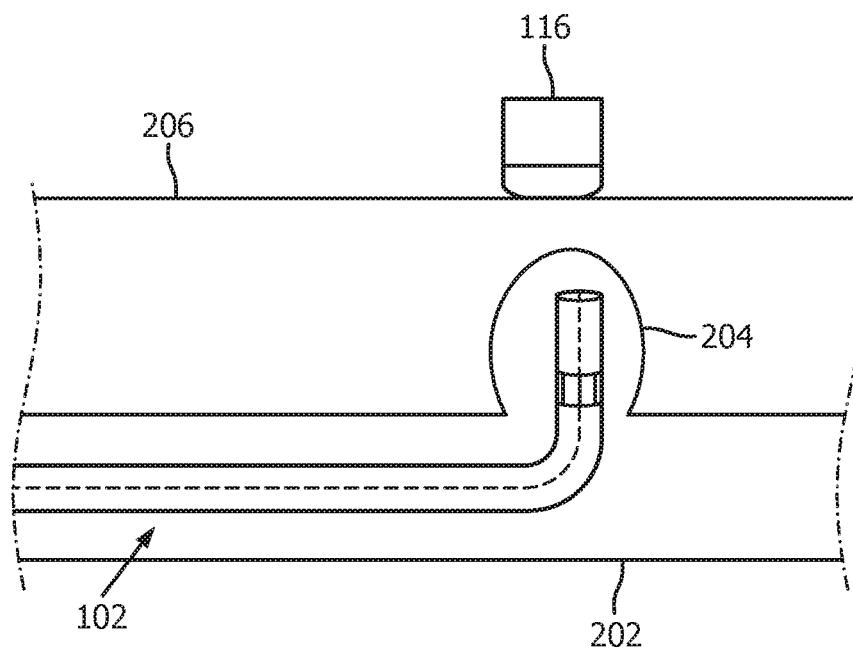
FIG. 2B is a diagrammatic, cross-sectional view of a portion of a subject's anatomy during an intravascular therapy according to various aspects of the present disclosure.

FIGS. 2A and 2B depict the arrival of the intravascular instrument 102 at a diseased location, e.g., aneurysm 204, of the blood vessel 202. The intravascular instrument 102 may obtain IVUS data, e.g., IVUS images, from within the blood vessel 202 at the site of the aneurysm 204 while the external ultrasound system 116 may obtain external ultrasound data from an extravascular position aligned with the aneurysm 204. In some cases, the IVUS data may comprise data about the inside of the aneurysm 204. In that regard, the intravascular instrument 102 may be positioned such that transmitted ultrasound signals from the transducer 104 reflect off the interior of the aneurysm 204. IVUS data about the inside of aneurysm 204 may sometimes be obtained by positioning the transducer 104 at the opening of the aneurysm as shown in FIG. 2A. Alternatively, IVUS data about the inside of aneurysm 204 may be obtained by advancing a distal portion of the intravascular instrument 102 containing the transducer 104 into the aneurysm 204 as shown in FIG. 2B. The IVUS data and the external ultrasound data may be sent to a medical processing system, e.g., the medical processing system 110, and may be used to create a 3D image of the aneurysm 204. In some cases, generation of the 3D image of the aneurysm 204 may depend on obtaining IVUS data about the interior of the aneurysm 204 and external ultrasound data from a location aligned with the aneurysm 204. As described herein, a medical processing system, e.g., medical processing system 110, may track progression of an intravascular therapy and may determine the likelihood that the intravascular therapy will be successful. In some cases, tracking progression of the intravascular therapy may depend on the ability to generate and analyze a 3D image of the aneurysm 204. Analyzing the 3D image may comprise comparing information gleaned from the 3D image with information contained in a database storing information about one or more intravascular therapies, including information about other intravascular therapies performed in the past. As of the state of the intravascular therapy in FIGS. 2A and 2B, the medical processing system may indicate that said therapy is 0% complete with 0% likelihood of success. Such determinations may be updated as the intravascular therapy, in this case an aneurysm coiling procedure, progresses.

Figure 2C:
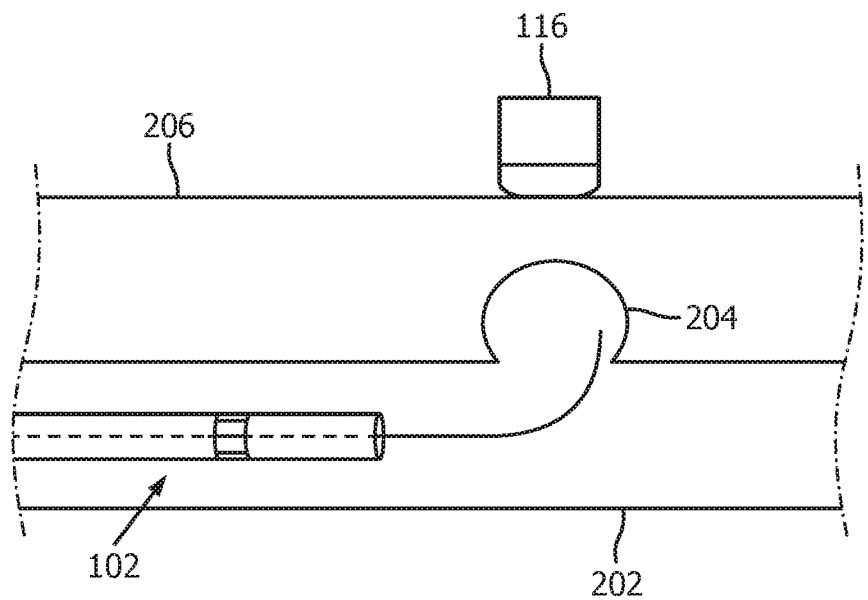
FIG. 2C is a diagrammatic, cross-sectional view of a portion of a subject's anatomy during an intravascular therapy according to various aspects of the present disclosure.
Figure 2D:
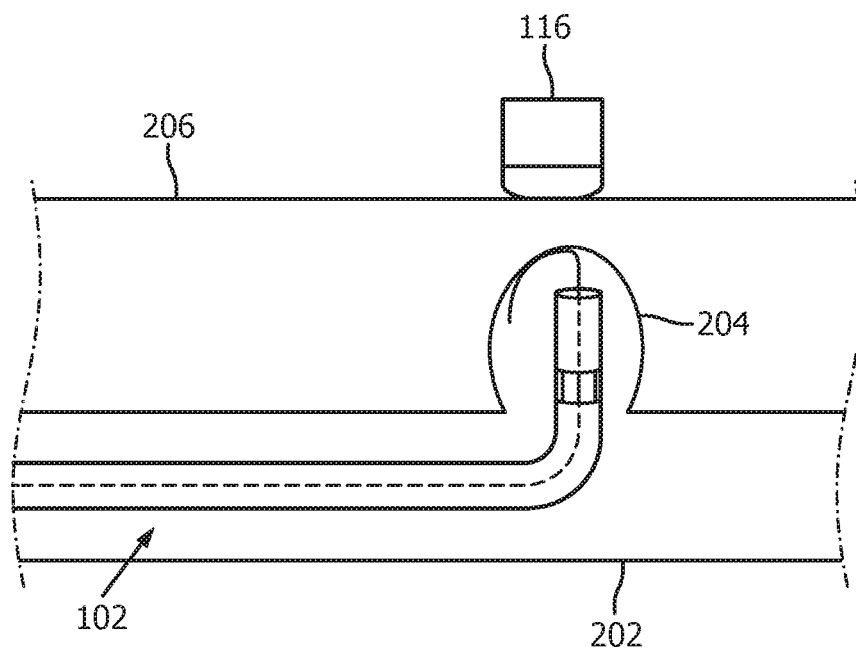
FIG. 2D is a diagrammatic, cross-sectional view of a portion of a subject's anatomy during an intravascular therapy according to various aspects of the present disclosure.

FIGS. 2C and 2D depict the beginning stages of an aneurysm coiling procedure. In that regard, the treatment device 106 may comprise one or more embolic coils. In the case of multiple coils, a coil may be detached from its delivery mechanism by an electrical pulse and/or by a cutting mechanism. The coils may comprise thin, flexible, metal strands of a material which stimulates the clotting process, e.g., platinum. The coils may comprise an echogenic material, e.g., calcium, to facilitate their resolution in an ultrasound image such as a 3D ultrasound image generated from IVUS data and external ultrasound data. The coils may be delivered into the aneurysm 204 while the intravascular instrument 102 is at a position outside the aneurysm 204, as shown in FIG. 2C, or alternatively may be delivered into the aneurysm 204 while a distal portion of the intravascular instrument 102 is positioned within the aneurysm 204, as shown in FIG. 2D.

Figure 2E:
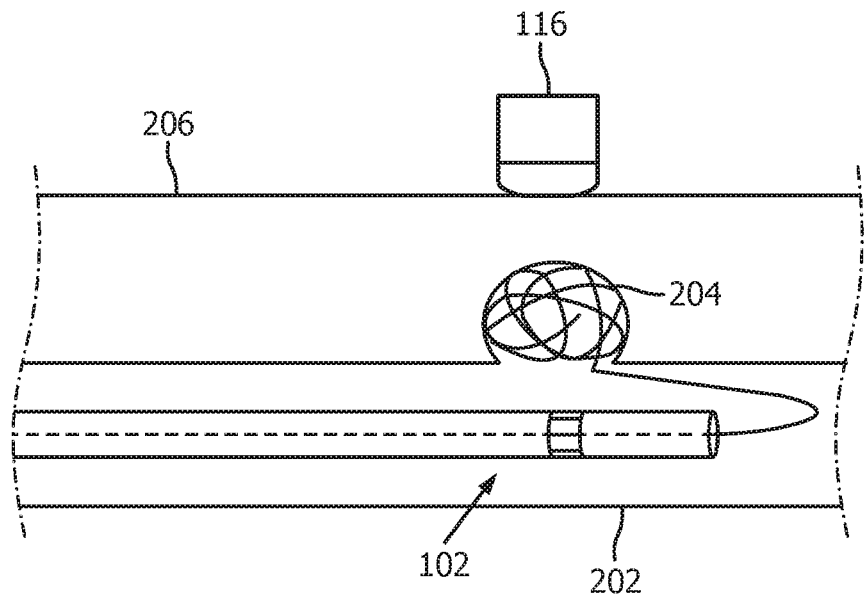
FIG. 2E is a diagrammatic, cross-sectional view of a portion of a subject's anatomy during an intravascular therapy according to various aspects of the present disclosure.
Figure 2F:
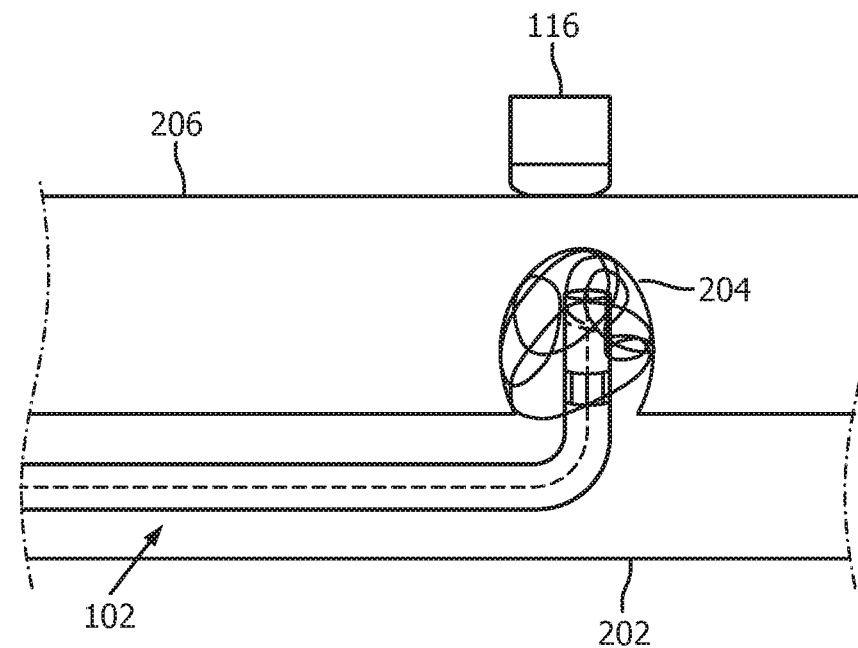
FIG. 2F is a diagrammatic, cross-sectional view of a portion of a subject's anatomy during an intravascular therapy according to various aspects of the present disclosure.

FIGS. 2E and 2F depict intermediate stages of an aneurysm coiling procedure. When coiling is performed from a location outside the aneurysm 204, as shown in FIG. 2E, the intravascular instrument 102 may be periodically adjusted from a coil delivery position to a position in which the transducer 104 is aligned with the opening of the aneurysm 204 in order to obtain IVUS data from within the aneurysm 204 to be used in combination with external ultrasound data to form 3D images of the aneurysm 204 to be used in determining the progress of the aneurysm coiling procedure. Such periodic adjustment may be unnecessary when coils are delivered into the aneurysm 204 while the distal portion of the intravascular instrument 102 is positioned within the aneurysm 204, as shown in FIG. 2F, because the transducer 104 may be able to successfully image the interior of the aneurysm 204 without such an adjustment. In some cases, even if coils are delivered while the distal portion of the intravascular instrument 102 is positioned within the aneurysm 204, it may be beneficial to adjust the position of the intravascular instrument 102 in order to obtain better images. Such adjustments may include removing the intravascular instrument 102 from a coil delivery position within the aneurysm 204 to a position outside the aneurysm 204 similar to that shown in FIG. 2E. Based on an analysis of the IVUS data and external ultrasound data obtained in FIGS. 2E and 2F, a medical processing system, e.g., medical processing system 110, may determine that the aneurysm coiling procedure is incomplete. The determination that the aneurysm coiling procedure is incomplete may be based on an analysis of a 3D image of the aneurysm 204 generated from the IVUS data and external ultrasound data. Accordingly, the intravascular instrument 102 may be returned to, or remain in, as the case may be, a coil delivery position to continue coiling.

Figure 2G:
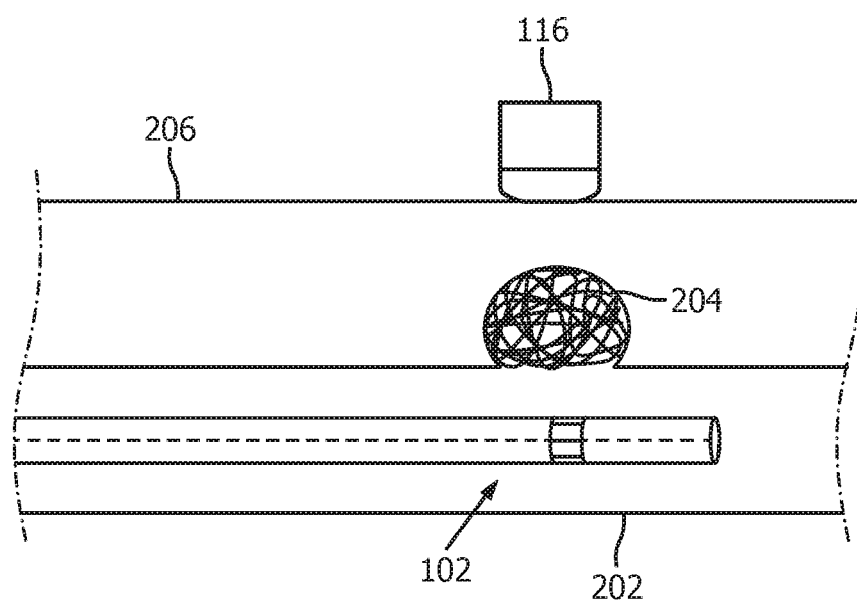
FIG. 2G is a diagrammatic, cross-sectional view of a portion of a subject's anatomy during an intravascular therapy according to various aspects of the present disclosure.

FIG. 2G depicts the final assessment of the aneurysm 204. The intravascular instrument 102 and the external ultrasound system 116 are positioned such that a 3D image of the aneurysm 204 may be generated. Based on an analysis of the 3D image, a medical processing system, e.g., medical processing system 110 may determine that the aneurysm coiling procedure is complete and may additionally determine the likelihood of success. Though not shown, the intravascular instrument 102 may be configured to place a stent or other scaffolding at the site of the aneurysm 204 to add stability to the region and help maintain the coils within the aneurysm 204. In some cases, adding the stent may be considered part of the aneurysm coiling procedure and may be factored into the likelihood that the aneurysm coiling procedure will be successful.

Figure 3:
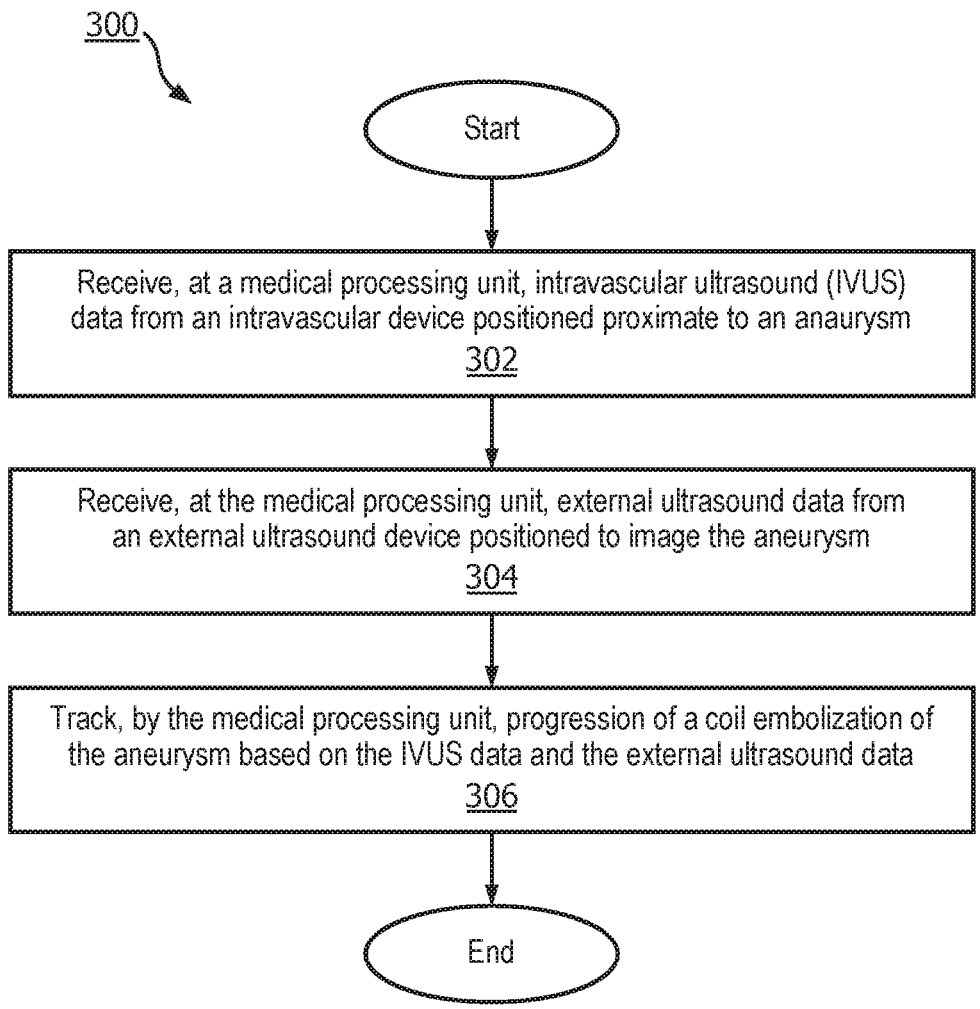
FIG. 3 is a flowchart of a method according to various aspects of the present disclosure.

Referring now to FIG. 3, shown therein is a flow chart of a method 300 according to embodiments of the disclosure. Portions of the method 300 may correspond to techniques discussed hereinabove with reference to FIGS. 1-2G and may be performed on, with, and/or by one or more elements of the system 100.

The method 300 begins at block 302 where intravascular ultrasound (IVUS) data may be received at a medical processing unit, e.g., medical processing system 110, from an intravascular device, e.g., intravascular instrument 102, positioned proximate to an aneurysm, e.g., aneurysm 204. At block 302, external ultrasound data may be received at the medical processing unit from an external ultrasound device, e.g., external ultrasound system 116, positioned to image the aneurysm. Progression of a coil embolization of the aneurysm may be tracked at block 306 by the medical processing unit based on the IVUS data and the external ultrasound data.

The method 300 may further comprise additional steps consistent with the foregoing disclosure. For example, the method 300 may comprise generating, by the medical processing unit, an image based on the IVUS data and the external ultrasound data. In some cases, generating the image may comprise combining the IVUS data and the external ultrasound data to generate a 3D image. The method 300 may comprise determining, by the medical processing unit, a probability of success for the coil embolization based on the IVUS data and the external ultrasound data. Further, the method 300 may omit some of the steps shown in FIG. 3 and/or perform the steps in various orders without departing from the scope of the present disclosure.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical system for use in conjunction with a subject who has an aneurysm, comprising:
an intravascular device including an intravascular ultrasound (IVUS) transducer configured to obtain IVUS data about an interior of the aneurysm from within vasculature of the subject including the aneurysm, wherein the intravascular device is configured to perform a coil embolization of the aneurysm using one or more coils comprising an echogenic material;
an external ultrasound system configured to obtain external ultrasound data about the aneurysm and the one or more coils from outside the subject; and
a computer processor configured to:
receive the IVUS data from the IVUS transducer, wherein the IVUS transducer is positioned within the vasculature proximate to the aneurysm;
receive the external ultrasound data acquired by the external ultrasound system while the IVUS transducer obtains the IVUS data about the interior of the aneurysm such that the external ultrasound data corresponds to the IVUS data, wherein the external ultrasound system is positioned outside of the subject at a location aligned with the intravascular device to image the aneurysm;
track progression and completion of the coil embolization of the aneurysm based on the IVUS data and the external ultrasound data; and
generate a three dimensional (3D) image based on the IVUS data and the external ultrasound data.

2. The medical system of claim 1, wherein the echogenic material comprises calcium.

3. The medical system of claim 1, wherein tracking progression of the coil embolization comprises:
analyzing the received IVUS data and the received ultrasound data, and comparing information gleaned from the analysis to information stored in a database storing information about past procedures.

4. The medical system of claim 1, wherein tracking progression of the coil embolization comprises monitoring the progress of the IVUS transducer toward a therapy site.

5. The medical system of claim 1, wherein tracking progression of the coil embolization comprises evaluating the completeness of the coil embolization.

6. A method, comprising:
receiving, at a computer processor, intravascular ultrasound (IVUS) data about interior of an aneurysm from an IVUS transducer of an intravascular device positioned proximate to the aneurysm within vascular that includes the aneurysm;
receiving, at the computer processor, external ultrasound data from an external ultrasound system positioned outside of the subject at a location aligned with the intravascular device to image the aneurysm, wherein the external ultrasound data is acquired while the IVUS transducer obtains the IVUS data about the interior of the aneurysm such that the external ultrasound data corresponds to the IVUS data;
delivering, with a treatment device comprising one or more embolic coils comprising an echogenic material, a coil embolization to the aneurysm, wherein the external ultrasound data includes the aneurysm and the one or more embolic coils; and
tracking, by the computer processor, progression of the coil embolization of the aneurysm by generating a three-dimensional (3D) image of the aneurysm based on the IVUS data about the interior of the aneurysm and the external ultrasound data.

7. The method of claim 6, wherein the echogenic material comprises calcium, the method further comprising generating, by the computer processor, the 3D image based on the IVUS data and the external ultrasound data.

8. The method of claim 7, wherein generating the 3D image comprises combining the IVUS data and the external ultrasound data.

9. The method of claim 6, wherein the IVUS data is obtained from within the aneurysm.

10. The method of claim 6, wherein the external ultrasound data is obtained from an extravascular position aligned with the aneurysm.

11. The method of claim 6, wherein tracking progression of the coil embolization includes monitoring the progress of the IVUS transducer toward a therapy site.

12. The method of claim 11, wherein monitoring the progress of the IVUS transducer comprises mapping the location of the IVUS transducer within a vessel.

13. The method of claim 6, wherein tracking progression of the coil embolization comprises evaluating the completeness of the coil embolization.

14. The method of claim 13, wherein evaluating the completeness of the coil embolization comprises determining a level of embolic coil occlusion within the aneurysm.

15. The method of claim 6, further comprising determining, by the computer processor, a probability of success for the coil embolization based on the IVUS data and the external ultrasound data.

16. A medical system, comprising:
an intravascular device including:
an intravascular ultrasound (IVUS) transducer positioned within vasculature including an aneurysm, wherein the IVUS transducer is proximate to the aneurysm and configured to obtain IVUS data about an interior of the aneurysm;
one or more treatment devices comprising one or more embolic coils comprising an echogenic material configured to deliver coil embolization of the aneurysm;
an external ultrasound system positioned outside of the subject at a location aligned with the intravascular device to image the aneurysm and the one or more embolic coils, and configured to obtain external ultrasound data,
a computer processor programmed to:
receive the IVUS data from the IVUS transducer,
receive the external ultrasound data acquired by the external ultrasound system while the IVUS transducer obtains the IVUS data about the interior of the aneurysm such that the received external ultrasound data corresponds to the IVUS data;
track progression of the coil embolization of the aneurysm based on the IVUS data and the external ultrasound data; and
generate a three dimensional (3D) image based on the IVUS data and the external ultrasound data.

17. The medical system of claim 16, wherein the computer processor is configured to track the progression of the coil embolization of the aneurysm based on the IVUS data and the external ultrasound data including:

determining the completion of the coil embolization of the aneurysm when blood flow to the aneurysm is reduced below a threshold.

18. The medical system of claim 16, wherein the computer processor is configured to track the progression of the coil embolization of the aneurysm based on the IVUS data and the external ultrasound data including:

determining the completion of the coil embolization of the aneurysm when coil fill of the aneurysm reaches a predefined percentage of the aneurysm.

* * * * *